United States Patent
Yoneyama et al.

(10) Patent No.: US 10,373,326 B2
(45) Date of Patent: Aug. 6, 2019

(54) BLOOD VESSEL IMAGE PROCESSING APPARATUS, BLOOD VESSEL IMAGE PROCESSING PROGRAM, AND BLOOD VESSEL IMAGE PROCESSING METHOD

(71) Applicant: PENTAS Inc., Tokyo (JP)

(72) Inventors: Shigeru Yoneyama, Tokyo (JP); Hiroyuki Takao, Tokyo (JP); Takashi Suzuki, Tokyo (JP); Yuichi Murayama, Tokyo (JP); Toshimitsu Furuchi, Tokyo (JP); Teppei Sakano, Tokyo (JP)

(73) Assignee: PENTAS Inc., Tokyo (JP)

( * ) Notice: Subject to any disclaimer, the term of this patent is extended or adjusted under 35 U.S.C. 154(b) by 0 days.

(21) Appl. No.: 15/742,492

(22) PCT Filed: Jun. 16, 2016

(86) PCT No.: PCT/JP2016/067881
§ 371 (c)(1),
(2) Date: Jan. 5, 2018

(87) PCT Pub. No.: WO2017/006732
PCT Pub. Date: Jan. 12, 2017

(65) Prior Publication Data
US 2018/0204339 A1  Jul. 19, 2018

(30) Foreign Application Priority Data
Jul. 9, 2015 (JP) .................................. 2015-137485

(51) Int. Cl.
*G06T 7/55* (2017.01)
*A61B 6/03* (2006.01)
(Continued)

(52) U.S. Cl.
CPC .............. *G06T 7/55* (2017.01); *A61B 5/0042* (2013.01); *A61B 5/02014* (2013.01);
(Continued)

(58) Field of Classification Search
None
See application file for complete search history.

(56) References Cited

U.S. PATENT DOCUMENTS 6,807,292 B1   10/2004  Goto et al.
2004/0249270 A1  12/2004  Kondo et al.
(Continued)

FOREIGN PATENT DOCUMENTS

JP   H11318884 A    11/1999
JP   2004283373 A2  10/2004
(Continued)

OTHER PUBLICATIONS

International Search Report dated Aug. 16, 2016 filed in PCT/JP2016/067881.
(Continued)

*Primary Examiner* — Fred H Hu
(74) *Attorney, Agent, or Firm* — Rankin, Hill & Clark LLP

(57) ABSTRACT

A control device defines, for three-dimensional blood vessel data of a blood vessel corresponding to a branched center line, a cylindrical coordinate system, thereby converting this into blood vessel data in an orthogonal coordinate system. The control device uses a coordinate value of the coordinate axis in a radial direction at a first coordinate value of the coordinate axis in a center line direction and a coordinate value of the coordinate axis in the radial direction at a second coordinate value of the coordinate axis in the center line direction, thereby interpolating a coordinate value of the coordinate axis in the radial direction between the first
(Continued)

coordinate value and the second coordinate value. The control device converts, after interpolation, the blood vessel data into blood vessel data in the cylindrical coordinate system.

12 Claims, 17 Drawing Sheets

(51) Int. Cl.
*A61B 5/00* (2006.01)
*A61B 5/02* (2006.01)
*A61B 5/107* (2006.01)
*A61B 5/055* (2006.01)
*A61B 6/00* (2006.01)
*G06T 7/00* (2017.01)

(52) U.S. Cl.
CPC ............ *A61B 5/055* (2013.01); *A61B 5/1076* (2013.01); *A61B 6/03* (2013.01); *A61B 6/032* (2013.01); *A61B 6/501* (2013.01); *A61B 6/504* (2013.01); *G06T 7/0012* (2013.01); *A61B 2576/026* (2013.01); *G06T 2207/30101* (2013.01); *G06T 2207/30172* (2013.01)

(56) References Cited

U.S. PATENT DOCUMENTS

| 2008/0160489 | A1 | 7/2008 | Bruijns | |
|---|---|---|---|---|
| 2012/0083696 | A1 | 4/2012 | Kitamura | |
| 2012/0201446 | A1* | 8/2012 | Yang | G06T 7/0012 382/134 |
| 2014/0163368 | A1 | 6/2014 | Rousso et al. | |
| 2014/0316758 | A1* | 10/2014 | Yagi | A61B 34/25 703/9 |
| 2016/0058422 | A1* | 3/2016 | Lee | A61B 8/4472 600/443 |
| 2017/0323587 | A1* | 11/2017 | Yagi | G06T 7/11 |
| 2017/0347966 | A1* | 12/2017 | Yagi | G16H 50/30 |

FOREIGN PATENT DOCUMENTS

| JP | 2008531108 A | 8/2008 | |
|---|---|---|---|
| JP | 2009268741 A2 | 11/2009 | |
| JP | 2010063670 A2 | 3/2010 | |
| JP | 2010178906 A2 | 8/2010 | |
| JP | 2012075702 A2 | 4/2012 | |
| JP | 2012110444 A2 | 6/2012 | |
| KR | 10-2014-01156 94 | * | 10/2014 |
| KR | 10-2014-0115694 | * | 10/2014 |
| WO | 2013031741 A1 | 3/2013 | |

OTHER PUBLICATIONS

Japanese Office Action dated Oct. 27, 2015 for the corresponding Japanese Patent Application No. 2015-137485.

* cited by examiner (a)

(b)

(c)

(a)

(b)

(a)

(b)

(a)

(b)

BLOOD VESSEL IMAGE PROCESSING APPARATUS, BLOOD VESSEL IMAGE PROCESSING PROGRAM, AND BLOOD VESSEL IMAGE PROCESSING METHOD

TECHNICAL FIELD

The present invention relates to a blood vessel image processing apparatus, a blood vessel image processing program, and a blood vessel image processing method.

BACKGROUND ART

The following aneurysm diagnosis support apparatus has been known. In this aneurysm diagnosis support apparatus, core line data is generated using, as a starting point, a reference point set within a brain artery region on three-dimensional image data, and a normal brain artery region and a cerebral aneurysm region are separated from each other based on continuity of the generated core line data. In this manner, a cerebral aneurysm is extracted (see Patent Literature 1).

CITATION LIST

Patent Literature

PATENT LITERATURE 1: JP-A-2012-110444

SUMMARY OF THE INVENTION

Problems to be Solved by the Invention

For removing a cerebral aneurysm, it is preferable that a normal main vessel shape is accurately grasped in advance. However, in the typical aneurysm diagnosis support apparatus, a cerebral aneurysm in the brain artery region can be extracted and specified, but no study has been conducted on the technique of specifying the normal main vessel shape.

Solution to the Problems

According to a first aspect of the present invention, a blood vessel image processing apparatus includes a center line specifying unit configured to specify a center line of a blood vessel based on three-dimensional blood vessel data showing the three-dimensional shape of the blood vessel; a protruding portion center line specifying unit configured to specify a center line of a protruding portion of the blood vessel from the center line specified by the center line specifying unit; a branched center line specifying unit configured to specify a center line branched from the protruding portion center line specified by the protruding portion center line specifying unit; a conversion unit configured to define, for the three-dimensional blood vessel data of the blood vessel corresponding to the branched center line specified by the branched center line specifying unit, a cylindrical coordinate system using, as coordinate axes, a blood vessel circumferential direction about the center line, a blood vessel radial direction from the center line, and a center line direction, thereby converting the blood vessel data in the cylindrical coordinate system into blood vessel data in an orthogonal coordinate system; an interpolation unit configured to use, on the blood vessel data converted into the orthogonal coordinate system by the conversion unit, a coordinate value of the coordinate axis in the radial direction at a first coordinate value of the coordinate axis in the center line direction and a coordinate value of the coordinate axis in the radial direction at a second coordinate value of the coordinate axis in the center line direction, thereby interpolating a coordinate value of the coordinate axis in the radial direction between the first coordinate value and the second coordinate value; and an inverse conversion unit configured to convert, after interpolation by the interpolation unit, the blood vessel data in the orthogonal coordinate system into blood vessel data in the cylindrical coordinate system.

According to a second aspect of the present invention, the blood vessel image processing apparatus according to the first aspect further includes a protruding portion data generation unit configured to calculate a difference between the three-dimensional blood vessel data and the blood vessel data in the cylindrical coordinate system after inverse conversion by the inverse conversion unit, thereby generating three-dimensional data of the protruding portion.

According to a third aspect of the present invention, in the blood vessel image processing apparatus according to the first or second aspect, the center line specifying unit narrows the blood vessel in a concentric fashion from an outer peripheral side to a center side based on the three-dimensional blood vessel data, and when a line reaches a predetermined line thickness, the line is specified as the center line.

According to a fourth aspect of the present invention, in the blood vessel image processing apparatus according to any one of the first to third aspects, the protruding portion center line specifying unit specifies a branching point of the center line for the center line specified by the center line specifying unit, and specifies, as the center line of the protruding portion of the blood vessel, a center line not having the branching point at least at one end.

According to a fifth aspect of the present invention, in the blood vessel image processing apparatus according to the fourth aspect, the protruding portion center line specifying unit excludes, from the center line specified by the center line specifying unit, a center line contacting the outer periphery of an image region of the three-dimensional blood vessel data, thereby specifying the protruding portion of the blood vessel.

According to a sixth aspect of the present invention, in the blood vessel image processing apparatus according to the fourth or fifth aspect, the protruding portion center line specifying unit specifies, as the length of the center line, a length from the branching point to a point at which the center line is disconnected, and excludes a center line with a value equal to or less than a predetermined threshold to specify the protruding portion of the blood vessel, the value being obtained in such a manner that the specified length of the center line is divided by a radius from the center line to the outer periphery of the blood vessel.

According to a seventh aspect of the present invention, a blood vessel image processing program causes a computer to execute the center line specifying process of specifying a center line of a blood vessel based on three-dimensional blood vessel data showing the three-dimensional shape of the blood vessel, the protruding portion center line specifying process of specifying a center line of a protruding portion of the blood vessel from the center line specified at the center line specifying process, the branched center line specifying process of specifying a center line branched from the protruding portion center line specified at the protruding portion center line specifying process, the conversion process of defining, for the three-dimensional blood vessel data of the blood vessel corresponding to the branched center line specified at the branched center line specifying process, a cylindrical coordinate system using, as coordinate axes, a blood vessel circumferential direction about the center line, a blood vessel radial direction from the center line, and a center line direction, thereby converting the blood vessel data in the cylindrical coordinate system into blood vessel data in an orthogonal coordinate system, the interpolation process of using, on the blood vessel data converted into the orthogonal coordinate system at the conversion process, a coordinate value of the coordinate axis in the radial direction at a first coordinate value of the coordinate axis in the center line direction and a coordinate value of the coordinate axis in the radial direction at a second coordinate value of the coordinate axis in the center line direction, thereby interpolating a coordinate value of the coordinate axis in the radial direction between the first coordinate value and the second coordinate value, and the inverse conversion process of converting, after interpolation at the interpolation process, the blood vessel data in the orthogonal coordinate system into blood vessel data in the cylindrical coordinate system.

According to an eighth aspect of the present invention, the blood vessel image processing program according to the seventh aspect further includes the protruding portion data generation process of calculating a difference between the three-dimensional blood vessel data and the blood vessel data in the cylindrical coordinate system after inverse conversion at the inverse conversion process, thereby generating three-dimensional data of the protruding portion.

According to a ninth aspect of the present invention, at the center line specifying process in the blood vessel image processing program according to the seventh or eighth aspect, the blood vessel is narrowed in a concentric fashion from an outer peripheral side to a center side based on the three-dimensional blood vessel data, and when a line reaches a predetermined line thickness, the line is specified as the center line.

According to a tenth aspect of the present invention, at the protruding portion center line specifying process in the blood vessel image processing program according to any one of the seventh to ninth aspects, a branching point of the center line is specified for the center line specified at the center line specifying process, and a center line not having the branching point at least at one end is specified as the center line of the protruding portion of the blood vessel.

According to an eleventh aspect of the present invention, at the protruding portion center line specifying process in the blood vessel image processing program according to the tenth aspect, a center line contacting the outer periphery of an image region of the three-dimensional blood vessel data is excluded from the center line specified at the center line specifying process, and the protruding portion of the blood vessel is specified.

According to a twelfth aspect of the present invention, at the protruding portion center line specifying process in the blood vessel image processing program according to the tenth or eleventh aspect, a length from the branching point to a point at which the center line is disconnected is specified as the length of the center line, and a center line with a value equal to or less than a predetermined threshold is excluded such that the protruding portion of the blood vessel is specified, the value being obtained in such a manner that the specified length of the center line is divided by a radius from the center line to an outer periphery of the blood vessel.

According to a thirteenth aspect of the present invention, a blood vessel image processing method includes the step of causing a center line specifying unit to specify a center line of a blood vessel based on three-dimensional blood vessel data showing a three-dimensional shape of the blood vessel; the step of causing a protruding portion center line specifying unit to specify a center line of a protruding portion of the blood vessel from the center line specified by the center line specifying unit; the step of causing a branched center line specifying unit to specify a center line branched from the protruding portion center line specified by the protruding portion center line specifying unit; the step of causing a conversion unit to define, for the three-dimensional blood vessel data of the blood vessel corresponding to the branched center line specified by the branched center line specifying unit, a cylindrical coordinate system using, as coordinate axes, a blood vessel circumferential direction about the center line, a blood vessel radial direction from the center line, and a center line direction, thereby converting the blood vessel data in the cylindrical coordinate system into blood vessel data in an orthogonal coordinate system; the step of causing an interpolation unit to use, on the blood vessel data converted into the orthogonal coordinate system by the conversion unit, a coordinate value of the coordinate axis in the radial direction at a first coordinate value of the coordinate axis in the center line direction and a coordinate value of the coordinate axis in the radial direction at a second coordinate value of the coordinate axis in the center line direction, thereby interpolating a coordinate value of the coordinate axis in the radial direction between the first coordinate value and the second coordinate value; and the step of causing an inverse conversion unit to convert, after interpolation by the interpolation unit, the blood vessel data in the orthogonal coordinate system into blood vessel data in the cylindrical coordinate system.

According to a fourteenth aspect of the present invention, the blood vessel image processing method according to the thirteenth aspect further includes the step of causing a protruding portion data generation unit to calculate a difference between the three-dimensional blood vessel data and the blood vessel data in the cylindrical coordinate system after inverse conversion by the inverse conversion unit, thereby generating three-dimensional data of the protruding portion.

According to a fifteenth aspect of the present invention, in the blood vessel image processing method according to the thirteenth or fourteenth aspect, the center line specifying unit narrows the blood vessel in a concentric fashion from an outer peripheral side to a center side based on the three-dimensional blood vessel data, and when a line reaches a predetermined line thickness, the line is specified as the center line.

According to a sixteenth aspect of the present invention, in the blood vessel image processing method according to any one of the thirteenth to fifteenth aspects, the protruding portion center line specifying unit specifies a branching point of the center line for the center line specified by the center line specifying unit, and specifies, as the center line of the protruding portion of the blood vessel, a center line not having the branching point at least at one end.

According to a seventeenth aspect of the present invention, in the blood vessel image processing method according to the sixteenth aspect, the protruding portion center line specifying unit excludes, from the center line specified by the center line specifying unit, a center line contacting the outer periphery of an image region of the three-dimensional blood vessel data, thereby specifying the protruding portion of the blood vessel.

According to an eighteenth aspect of the present invention, in the blood vessel image processing method according the sixteenth or seventeenth aspect, the protruding portion center line specifying unit specifies, as the length of the center line, a length from the branching point to a point at which the center line is disconnected, and excludes a center line with a value equal to or less than a predetermined threshold to specify the protruding portion of the blood vessel, the value being obtained in such a manner that the specified length of the center line is divided by a radius from the center line to an outer periphery of the blood vessel.

Effects of the Invention

According to the present invention, on the blood vessel data of the blood vessel in the orthogonal coordinate system corresponding to the center line branched from the protruding portion center line, the coordinate value of the coordinate axis in the radial direction at the first coordinate value of the coordinate axis in the center line direction and the coordinate value of the coordinate axis in the radial direction at the second coordinate value of the coordinate axis in the center line direction are used to interpolate the coordinate value of the coordinate axis in the radial direction between the first coordinate value and the second coordinate value, and after interpolation, the blood vessel data in the orthogonal coordinate system is converted into the blood vessel data in the cylindrical coordinate system. Thus, normal main vessel three-dimensional data showing the blood vessel from which the protruding portion has been removed is generated, and as a result, a normal main vessel shape can be specified.

DESCRIPTION OF THE EMBODIMENTS

Figure 1:
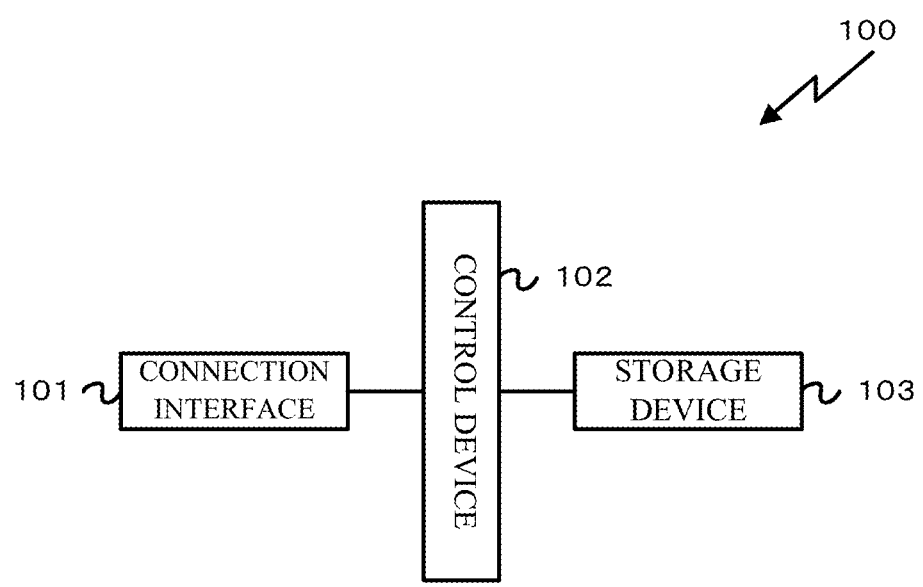
FIG. 1 is a block diagram of a configuration of one embodiment of a blood vessel image processing apparatus 100.

FIG. 1 is a block diagram of a configuration of one embodiment of a blood vessel image processing apparatus 100 of the present embodiment. For example, an image processing apparatus, such as a server apparatus or a personal computer, in which a program for performing image processing of a blood vessel image is installed, is used as the blood vessel image processing apparatus 100. FIG. 1 illustrates the configuration of one embodiment in the case of using the server apparatus as the blood vessel image processing apparatus 100. The blood vessel image processing apparatus 100 includes a connection interface 101, a control device 102, and a storage device 103.

The connection interface 101 is an interface for connecting the blood vessel image processing apparatus 100 to other apparatuses or external equipment such as a terminal. The connection interface 101 includes, for example, an interface for connecting the blood vessel image processing apparatus 100 to a display apparatus such as a liquid crystal display, and an interface for connecting the blood vessel image processing apparatus 100 to a communication line such as the LAN or the Internet. In a case where the connection interface 101 is the interface for connecting the blood vessel image processing apparatus 100 to the display apparatus such as the liquid crystal display, information is output to a monitor connected to the connection interface 101 so that the information can be displayed on the monitor. Alternatively, in a case where the connection interface 101 is the interface for connecting the blood vessel image processing apparatus 100 to the communication line such as the LAN or the Internet, communication with other apparatuses or equipment connected to the communication line can be made via the connection interface 101.

The control device 102 includes a CPU, a memory, and other peripheral circuits, and is configured to control the entirety of the blood vessel image processing apparatus 100. Note that the memory forming the control device 102 is a volatile memory such as a SDRAM. This memory is used as a work memory for expanding the program upon execution of the program by the CPU or a buffer memory for temporarily storing data.

The storage device 103 is a storage device for storing, e.g., various types of data stored in the blood vessel image processing apparatus 100 and program data for execution by the control device 102. For example, a hard disk drive (HDD) or a solid state drive (SSD) is used as the storage device 103. Note that the program data stored in the storage device 103 is provided with the program data being stored in a storage medium such as a CD-ROM or a DVD-ROM, or is provided via a network. An operator acquires and installs the program data in the storage device 103 so that the control device 102 can execute the program.

The blood vessel image processing apparatus 100 of the present embodiment performs the processing of specifying a blood vessel abnormally-protruding region based on three-dimensional image data of a blood vessel stored in advance in the storage device 103, thereby specifying a normal main vessel shape after removal of the specified abnormally-protruding region. In the present embodiment, an example in a case where three-dimensional blood vessel data acquired by photographing of a brain blood vessel is stored in advance in the storage device 103 to detect a blood vessel abnormally-protruding region such as a cerebral aneurysm as one of cerebral vascular diseases will be described.

The three-dimensional blood vessel data stored in the storage device 103 is generated based on image data acquired by photographing upon diagnosis of a patient. In general, upon diagnosis of a blood vessel disease such as a cerebral aneurysm, diagnostic photographing is performed by computed tomography angiography (CTA), three-dimensional digital subtraction angiography (3D-DSA), or magnetic resonance angiography (MRA), and such an acquired image is saved as image data according to digital imaging and communication in medicine (DICOM) standards. Upon diagnostic photographing, many sectional layers of a photographing target (e.g., a head) are photographed. Thus, these sectional layer images are overlapped with each other, thereby producing three-dimensional image data of the photographing target.

In the present embodiment, the three-dimensional blood vessel data acquired by extraction of only a blood vessel shape from the three-dimensional image data of the photographing target acquired by photographing as described above is stored in the storage device 103. For example, the following method is conceivable as the method for producing the three-dimensional blood vessel data by extraction of only the blood vessel shape from the three-dimensional image data of the photographing target.

In each of the above-described sectional layer images, the photographing target is displayed with different color densities according to materials. Thus, when image data of a region formed of pixels corresponding to a blood vessel color density can be extracted from the three-dimensional image data of the photographing target, the three-dimensional blood vessel data only with the extracted blood vessel shape can be produced. The color density in the three-dimensional image data of the photographing target is, based on a photographing principle of each modality, determined by numerical information acquired upon photographing. For example, in the case of the CTA, absorbability of an X-ray, i.e., X-ray transmittance, is detected for photographing. The X-ray transmittance is represented by a CT value (in units of HU) when water is taken as 0 and air is taken as −1000, and the color density is determined by the magnitude of such a value. That is, in the three-dimensional image data of the photographing target acquired by the CTA, a value of about −2048 to about +2000 is assigned to each pixel according to the X-ray transmittance.

For example, a range of numerical value corresponding to the blood vessel color density is set in advance, and image processing is performed for the three-dimensional image data of the photographing target such that a pixel with a pixel value equal to or less than the lower limit of the range is converted into white and a pixel with a pixel value equal to or greater than the upper limit of the range is converted into black. Thus, the three-dimensional image data can be acquired, in which the color density upon photographing can be held for pixels with numerical pixel values corresponding to the blood vessel color density and other pixels are converted into white and black. Consequently, the blood vessel region can be extracted from the three-dimensional image data of the photographing target. A threshold for the pixel value for extraction of the blood vessel region as described herein varies according to individual patients, and for this reason, a value suitable for each patient is preferably set upon execution of the processing.

Figure 2:
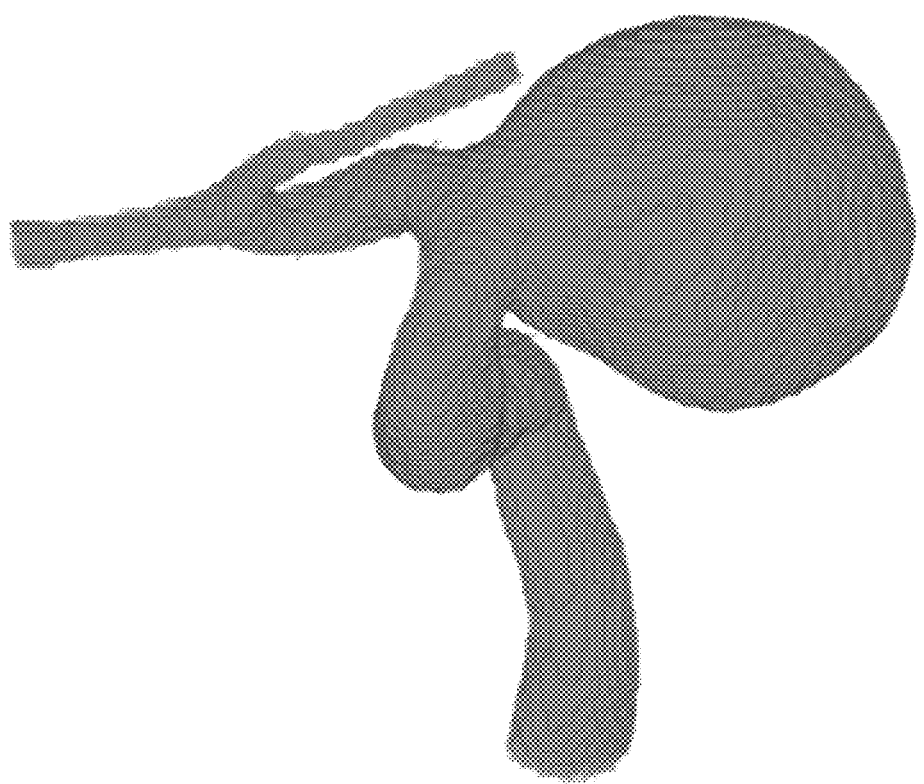
FIG. 2 is a schematic view of an example of three-dimensional blood vessel data.

In the present embodiment, voxel data showing the inside of the extracted blood vessel region, i.e., an intravascular lumen, filled with voxels is stored as the three-dimensional blood vessel data in the storage device 103. FIG. 2 is a schematic view of an example of the three-dimensional blood vessel data stored in the storage device 103.

The control device 102 reads the three-dimensional blood vessel data from the storage device 103, thereby producing a center line passing through the center of the blood vessel. In the three-dimensional blood vessel data, the blood vessel is photographed in a substantially cylindrical shape. Thus, in the present embodiment, the voxel data is scraped starting from the outside, and the remaining voxels at a center portion are connected together to produce the center line. That is, the control device 102 narrows the blood vessel in a concentric fashion from an outer peripheral side to a center side based on the three-dimensional blood vessel data. When a line thickness reaches a predetermined thickness set in advance, such a line is specified as the center line.

Figure 3:
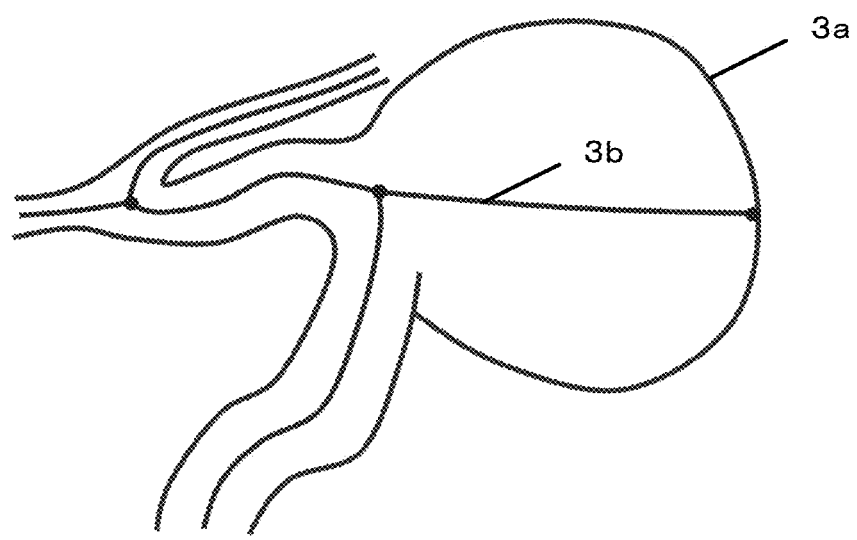
FIG. 3 is a schematic view of a center line of a blood vessel produced for the three-dimensional blood vessel data.

FIG. 3 is a schematic view of the center line of the blood vessel produced for the three-dimensional blood vessel data. In an example illustrated in FIG. 3, a center line 3b is produced for a blood vessel 3a.

Figure 4:
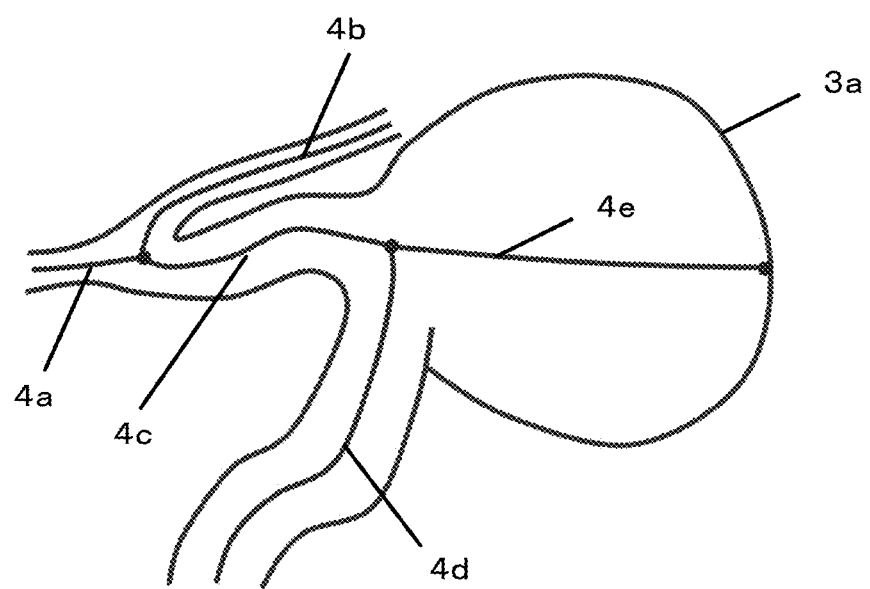
FIG. 4 is a view of a specific example in the case of specifying individual center lines based on branching points.

In the present embodiment, the control device 102 specifies points at which the produced center line is branched, and as individual center lines, specifies a center line between the branching points and a center line between the branching point and a point at which the center line is disconnected. Thus, the center line 3b illustrated in FIG. 3 is separated into five center lines 4a to 4e as illustrated in FIG. 4. In the following processing, these center lines 4a to 4e will be referred to as "center lines," and are targeted for processing.

Based on the produced center lines, the control device 102 specifies a blood vessel protruding portion which is highly likely to be the abnormally-protruding region such as an aneurysm. The control device 102 specifies, as a center line of the protruding portion, a center line having no branching point at one end. Note that the control device 102 excludes, from specifying candidates, a center line with one end contacting the outer periphery of an image region of the three-dimensional blood vessel data even when such a center line has no branching point at one end. Moreover, the control device 102 excludes, from the specifying candidates, a center line of a thin blood vessel disconnected in the middle even when such a center line has no branching point at one end. Determination on whether or not the center line is the center line of the thin blood vessel disconnected in the middle is made as follows.

The control device 102 specifies, as the length L1 of the center line, a length from the branching point to the point at which the center line is disconnected, and determines, as the center line of the thin blood vessel disconnected in the middle, a center line with a small ratio between the specified length L1 of the center line and a radius L2 from the center line to the outer periphery of the blood vessel. For example, a value is obtained in such a manner that the length L1 of the center line is divided by the radius L2 from the center line to the outer periphery of the blood vessel. When such a value is equal to or less than a predetermined threshold of, e.g., 10, the center line is determined as the center line of the thin blood vessel disconnected in the middle, and is excluded.

Note that in the present embodiment, a distance from the center line to a blood vessel wall is calculated for each position on the center line in an entire circumferential direction of the blood vessel, and the average of these values is specified as the radius L2 from the center line to the outer periphery of the blood vessel. The number of samples for calculation of the average, i.e., the number of blood vessel pieces divided in the entire circumferential direction for calculation of the distance from the center line to the blood vessel wall, is set in advance. As an example, the following method is conceivable; the blood vessel is divided into 12 pieces at intervals of 30 degrees, and the distance from the center line to the blood vessel wall is calculated for 12 directions; and thus, the average of these values is calculated to obtain the radius L2 from the center line to the outer periphery of the blood vessel.

Figure 5:
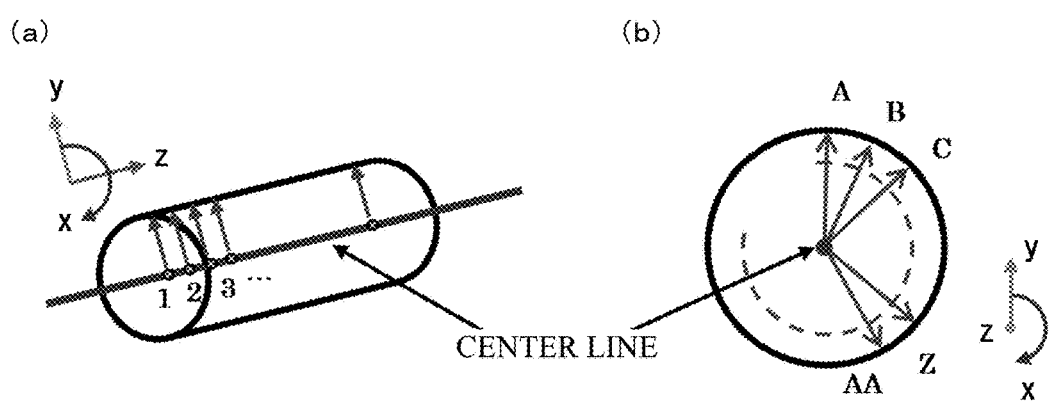
FIG. 5 is a schematic view of the method for calculating a radius from the center line to the outer periphery of the blood vessel based on the three-dimensional blood vessel data.

FIG. 5 is a schematic view of the method for calculating the radius L2 from the center line to the outer periphery of the blood vessel based on the three-dimensional blood vessel data. In the present embodiment, the radius from the center line to the outer periphery of the blood vessel is calculated for each position on the center line, each position being indicated by numbers of 1, 2, 3, . . . as illustrated in FIG. 5(a). The interval between the positions on the center line is determined in advance. As illustrated in FIG. 5(b), the radius from the center line to the outer periphery of the blood vessel at each position on the center line is specified in such a manner that a distance from the center line to each point on the outer periphery of the blood vessel as indicated by A, B, . . . , Z, AA and the average of these values is calculated. The control device 102 averages the radius specified for each position on the center line, thereby calculating the radius L2 from the center line of the blood vessel to the outer periphery of the blood vessel.

Figure 6:
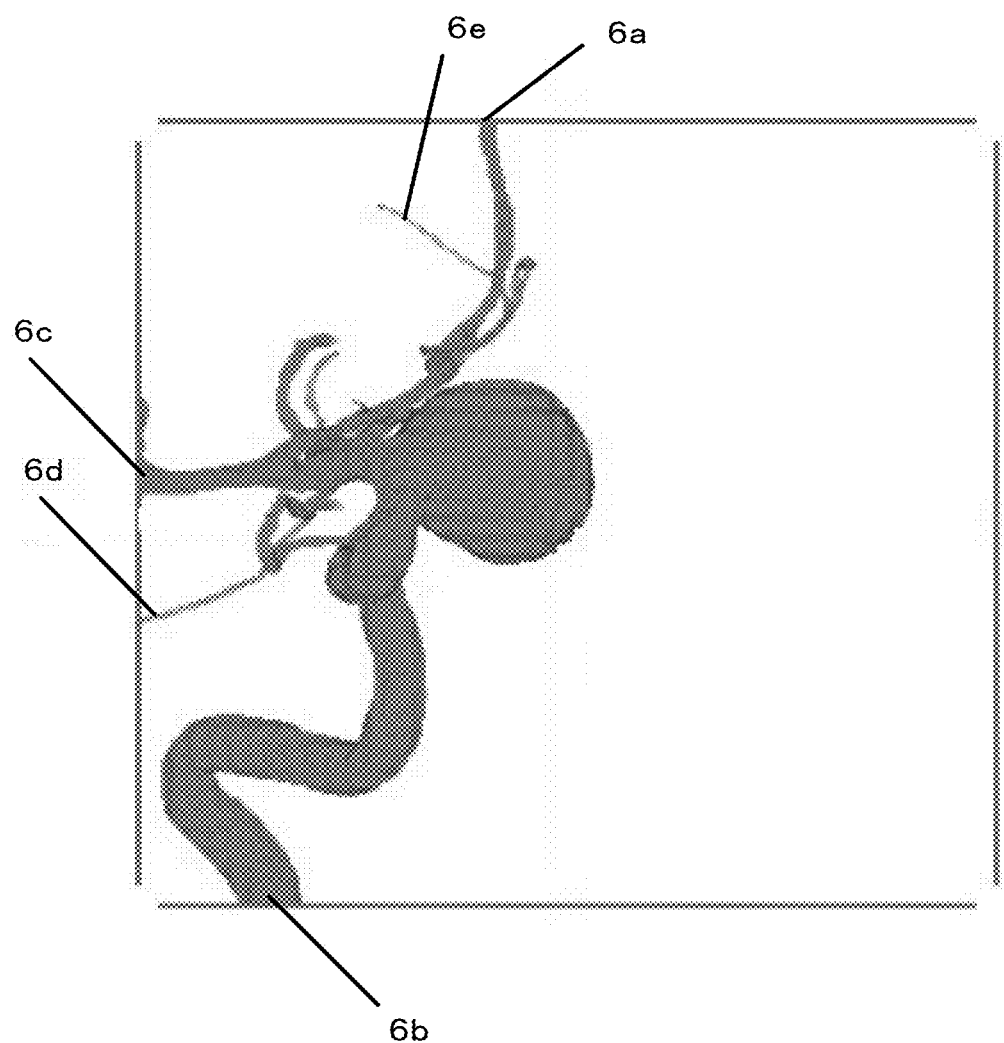
FIG. 6 is a view of a specific example of blood vessels whose center lines contact, at one ends thereof, the outer periphery of an image region of the three-dimensional blood vessel data and a thin blood vessel whose center line is disconnected in the middle.

By the above-described processing, blood vessels 6a, 6b, 6c, 6d whose center lines contact, at one ends thereof, the outer periphery of the image region of the three-dimensional blood vessel data and a thin blood vessel 6e whose center line is disconnected in the middle are, as illustrated in FIG. 6, excluded from the specifying candidates for the protruding portion, for example.

Figure 7:
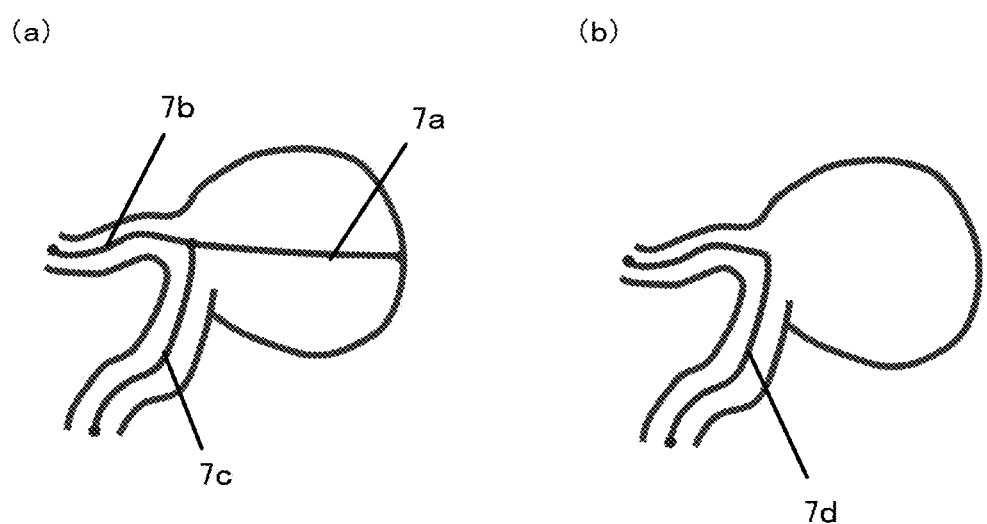
FIG. 7 is a schematic view of an example of a specified center line of a protruding portion and an example of specified branched center lines.

The control device 102 can specify, by the above-described processing, the center line of the blood vessel which is highly likely to be the abnormally-protruding region such as an aneurysm, i.e., the center line of the protruding portion. In the present embodiment, the following processing will be described with reference to an example case where a center line 7a illustrated in FIG. 7(a) is, by the above-described processing, specified as the center line of the blood vessel which is highly likely to be the abnormally-protruding region such as an aneurysm, i.e., the center line of the protruding portion. Note that in the present embodiment, the processing for the center line 7a will be described. However, in a case where multiple center lines are specified as protruding portion center lines by the above-described processing, the later-described processing is executed for each protruding portion center line.

The control device 102 specifies center lines branched from the center line 7a of the protruding portion. In the example illustrated in FIG. 7(a), two center lines 7b, 7c are specified as the center lines branched from the center line 7a of the protruding portion. The control device 102 re-defines, as a single center line, the center lines branched from the center line 7a of the protruding portion, and uses such a center line for subsequent processing. Thus, the center line 7b and the center line 7c are re-defined as a single center line 7d as illustrated in FIG. 7(b). In description below, the re-defined center line 7d will be referred to as a "branched center line," and will be distinguished from the above-described center lines.

Figure 8:
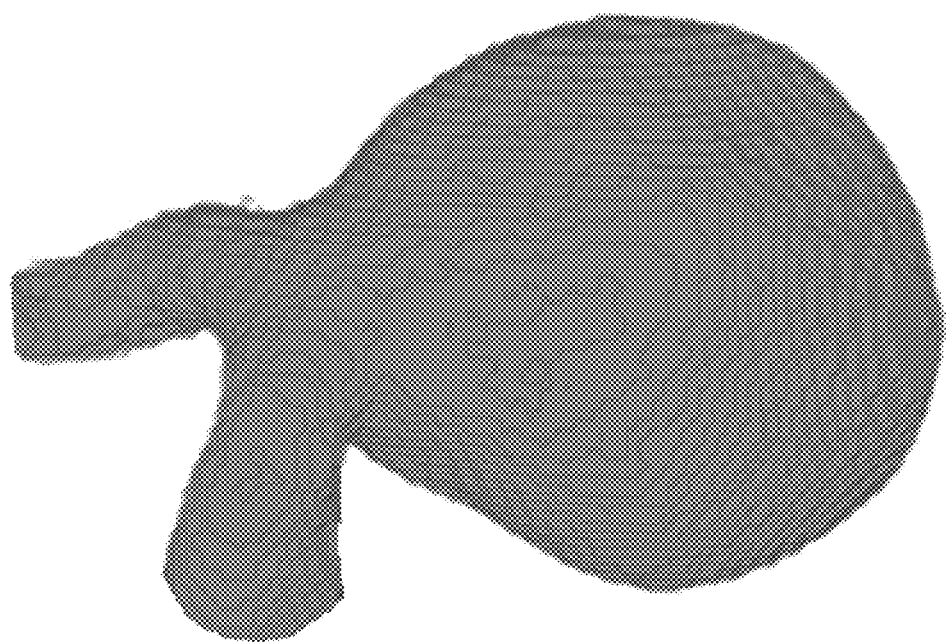
FIG. 8 is a view of a specific example of processing target voxel data.

The control device 102 reads, from the storage device 103, three-dimensional blood vessel data of a region including the re-defined branched center line 7d. Thus, e.g., voxel data of a blood vessel illustrated in FIG. 8 is read as the three-dimensional blood vessel data of the region including the branched center line 7d.

Figure 9:
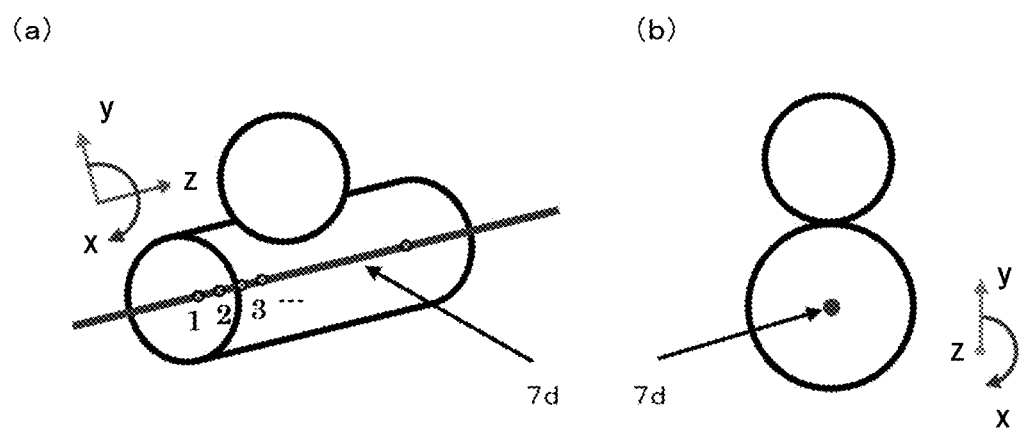
FIG. 9 is a schematic view of an example of a defined cylindrical coordinate system for the processing target voxel data.

The control device 102 takes, as processing target voxel data, the three-dimensional blood vessel data of the region including the branched center line 7d, and for the processing target voxel data, performs voxel data expansion processing with reference to the branched center line 7d. The voxel data expansion processing will be described herein. For the processing target voxel data, the control device 102 defines a cylindrical coordinate system using, as coordinate axes, a blood vessel circumferential direction about the center line, a blood vessel radial direction from the center line, and a center line direction. FIG. 9 is a schematic view of a specific example in a case where a cylindrical coordinate system is defined for the processing target voxel data such that a blood vessel circumferential direction about the branched center line 7d is taken as a x-axis, a blood vessel radial direction from the branched center line 7d is taken as a y-axis, and a branched center line 7d direction is taken as a z-axis. Note that FIG. 9(a) is a view of a state of the processing target voxel data in a diagonal direction. FIG. 9(b) is a view of a state of the processing target voxel data in the branched center line 7d direction, i.e., a z-axis direction.

The control device 102 converts the processing target voxel data in the cylindrical coordinate system as illustrated in FIG. 9 into blood vessel data in an orthogonal coordinate system. In the present embodiment, the control device 102 plots each point of the processing target voxel data on the orthogonal coordinate system in which a point at an angle of 0° in the blood vessel circumferential direction about the branched center line 7d is taken as an origin of the x-axis, a point on the branched center line 7d is taken as an origin of the y-axis, and one end point of the branched center line 7d is taken as an origin of the z-axis. In this manner, the control device 102 converts the processing target voxel data into the blood vessel data in the orthogonal coordinate system. Thus, the voxel data acquired by expansion of the processing target voxel data in the cylindrical coordinate system into the orthogonal coordinate system can be acquired. Note that in a coordinate system (hereinafter referred to as a "global coordinate system") taken over from an original image, the origin of the x-axis for the blood vessel data in the orthogonal coordinate system is defined in the direction of cross product between a vector in a center line axial direction and a y-axis direction vector of the global coordinate system of the three-dimensional blood vessel data. When the vector in the center line axial direction and the y-axis direction vector of the global coordinate system are coincident with each other, a z-axis direction vector is used instead of a y-axis direction.

Figure 10:
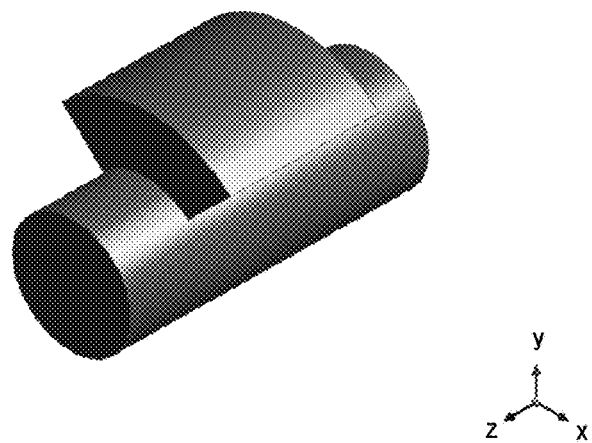
FIG. 10 is a schematic view of the processing target voxel data.
Figure 10:
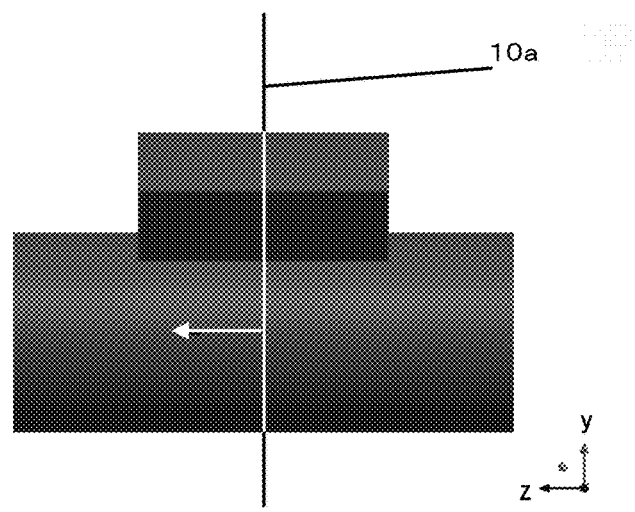
Figure 10:
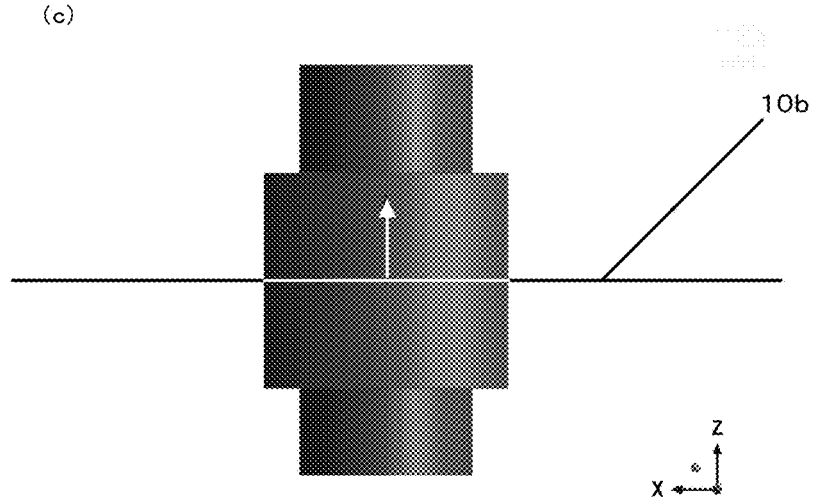

An example where the processing target voxel data is expanded into the voxel data in the orthogonal coordinate system will be described with reference to FIGS. 10 to 14. FIG. 10 is a schematic view for describing the processing target voxel data. FIG. 10(a) is a perspective view of the processing target voxel data. FIG. 10(b) is a view of the processing target voxel data in a direction in which the angle of the blood vessel circumferential direction about the branched center line 7d is 180°. FIG. 10(c) is a view of the processing target voxel data in a direction in which the angle of the blood vessel circumferential direction about the branched center line 7d is 270°. In the processing target voxel data illustrated in FIG. 10, the shape of a cylindrical blood vessel with a fan-shaped protruding portion present on the blood vessel is schematically illustrated.

Figure 11:
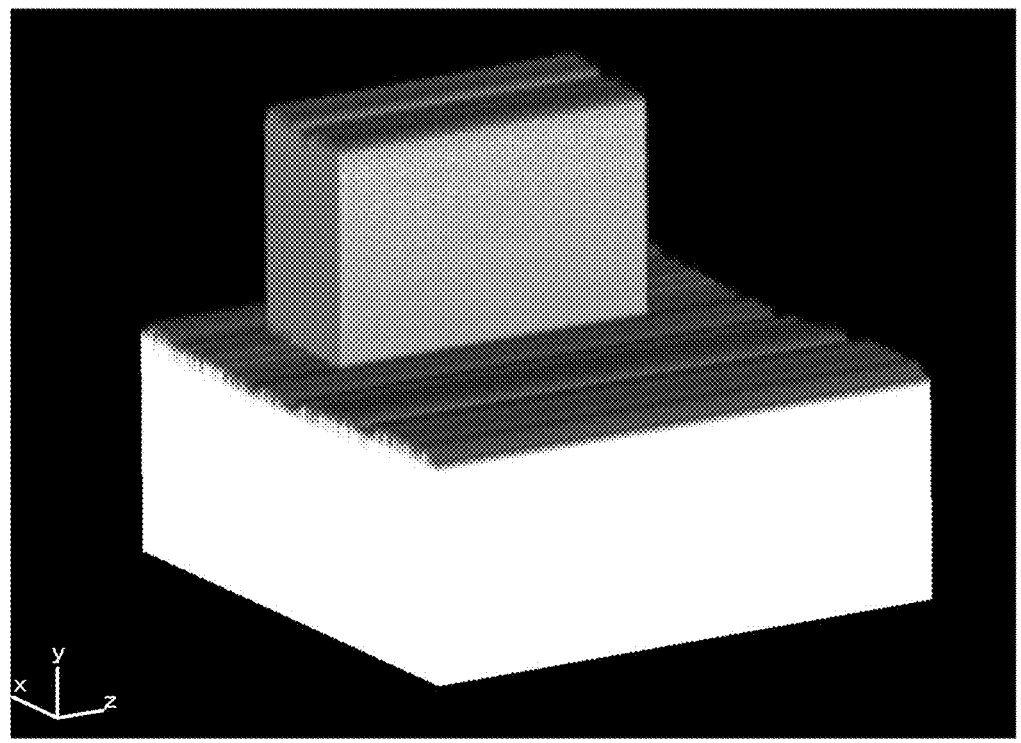
FIG. 11 is a schematic view of a result of expansion of the processing target voxel data into voxel data in an orthogonal coordinate system.
Figure 12:
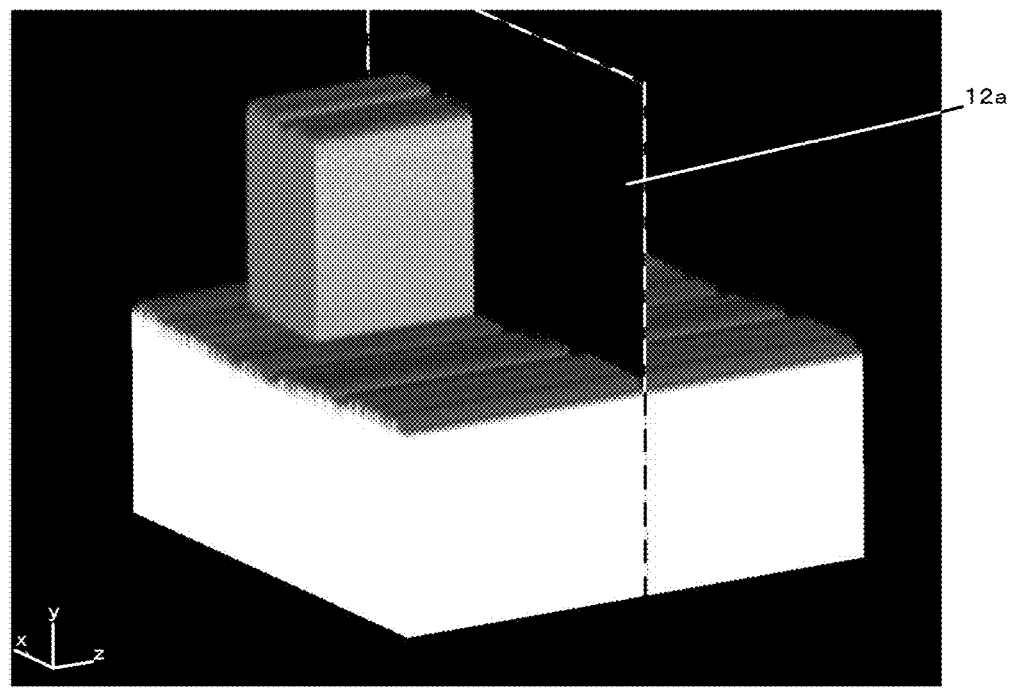
FIG. 12 is a first view of a section of the expanded voxel data.
Figure 12:
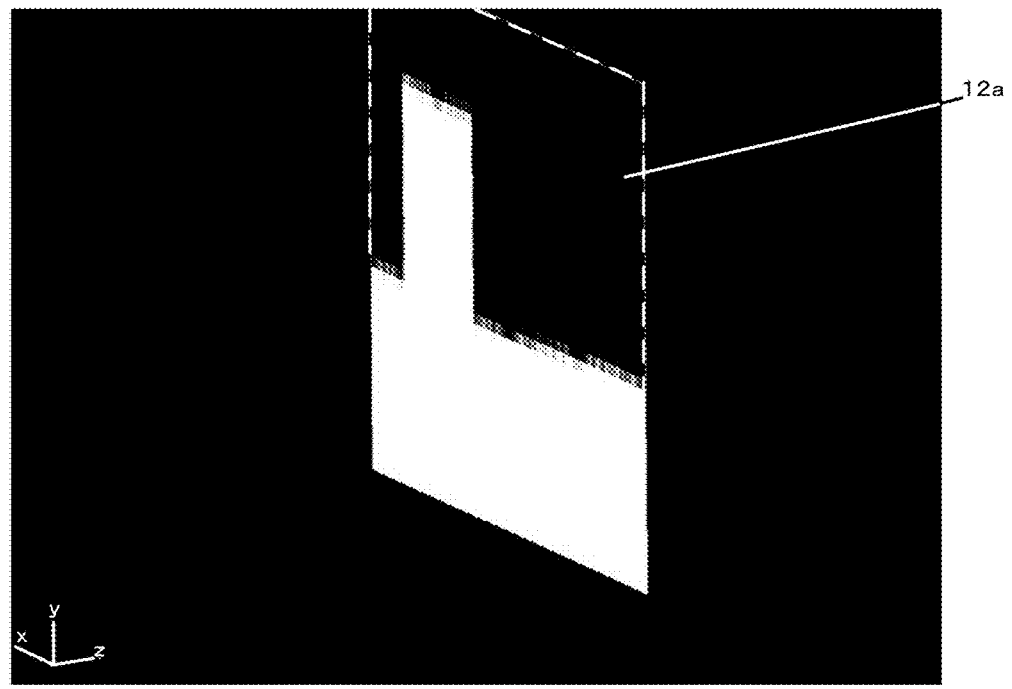
Figure 13:
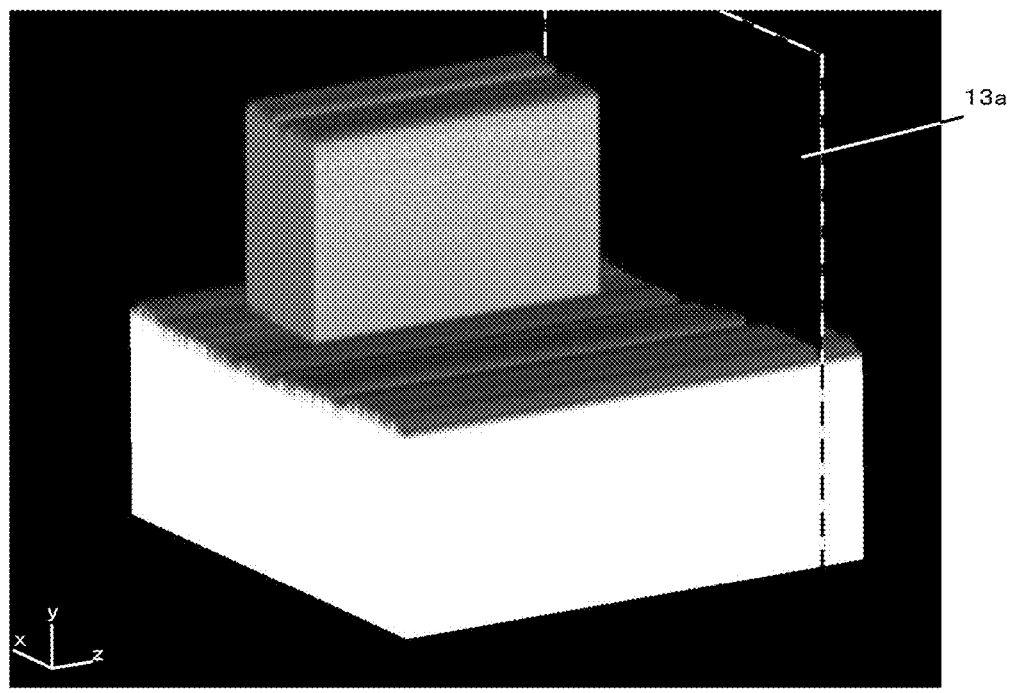
FIG. 13 is a second view of a section of the expanded voxel data.
Figure 13:
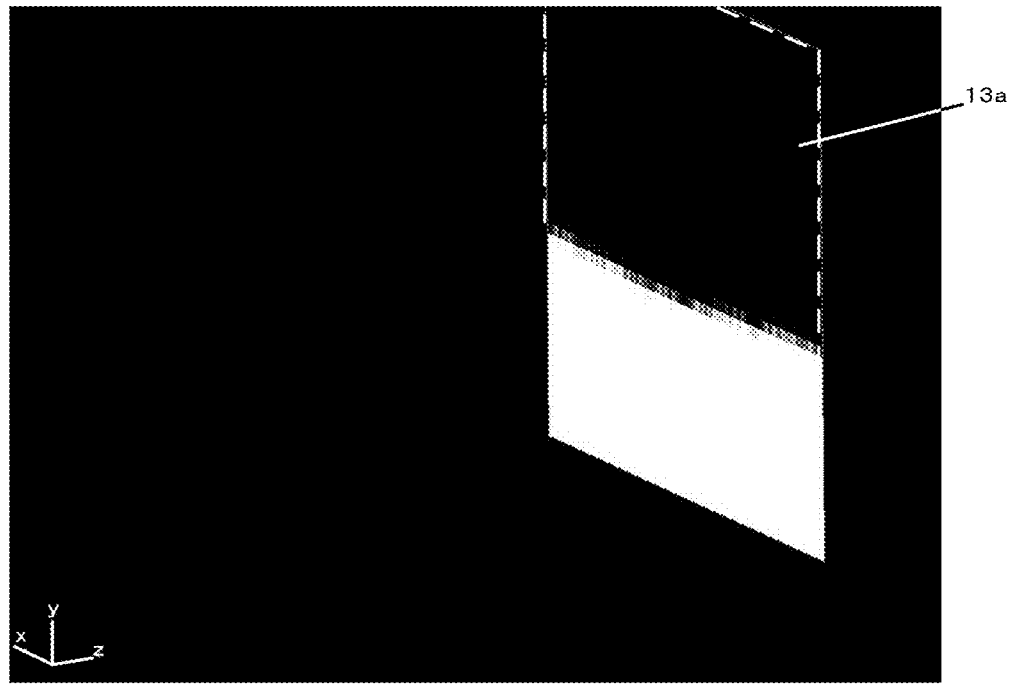

FIG. 11 is a schematic view of a result of expansion of the processing target voxel data illustrated in FIG. 10 into the voxel data in the orthogonal coordinate system. As illustrated in FIG. 11, in the expanded voxel data after expansion into the orthogonal coordinate system, a y-value of a region of the processing target voxel data illustrated in FIG. 10 corresponding to the fan-shaped protruding portion is great, and therefore, such a portion also protrudes in the y-axis direction in the expanded voxel data.

A sectional view in a case where the expanded voxel data illustrated in FIG. 11 is cut along a cut plane 12a indicated by a dashed line in FIG. 12(a) is illustrated in FIG. 12(b). The cut plane 12a is set to a z-position of the expanded voxel data including the protruding portion, and therefore, the protruding portion is shown in the y-axis direction in the sectional view of FIG. 12(b).

A sectional view in a case where the expanded voxel data illustrated in FIG. 11 is cut along a cut plane 13a indicated by a dashed line in FIG. 13(a) is illustrated in FIG. 13(b). The cut plane 13a is set to a z-position of the expanded voxel data not including the protruding portion, and therefore, the protruding portion is not shown in the y-axis direction in the sectional view of FIG. 13(b).

Figure 14:
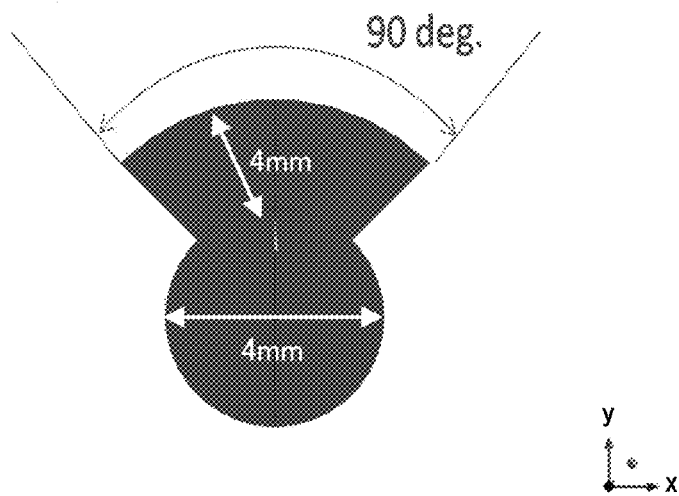
FIG. 14 is a view with a dimension example of the processing target voxel data.
Figure 14:
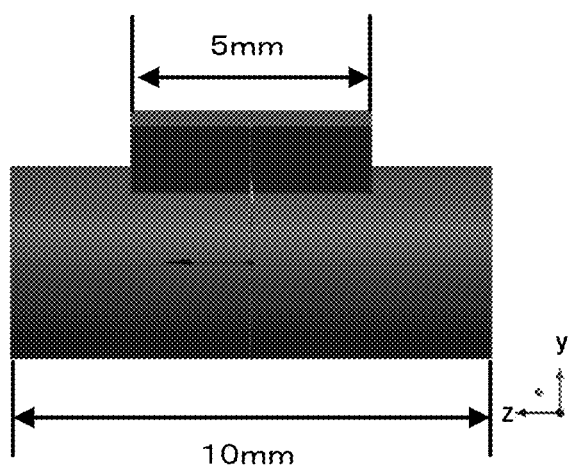

FIG. 14 is a view with the dimensions of the processing target voxel data illustrated in FIG. 10. Note that the dimensions added to this figure are added as examples for description, and do not precisely show actual dimensions. FIG. 14(a) illustrates a section in a case where the processing target voxel data illustrated in FIG. 10 is cut along a cut line 10a illustrated in FIG. 10(b) and a cut line 10b illustrated in FIG. 10(c), the view showing a state in the direction of an arrow added to each of the cut lines 10a, 10b. FIG. 14(b) is a view of the processing target voxel data of FIG. 10(b) with the dimensions.

With the added dimensions illustrated in FIG. 14(a), the height of a portion with a small value in the y-axis direction is, in the sectional view illustrated in FIG. 12(b), equivalent to 2 mm, and the height of a portion with a great value in the y-axis direction is equivalent to 6 mm. Moreover, in the sectional view illustrated in FIG. 12(b), a value in a x-axis direction corresponds to the angle of opening of the fan-shaped protruding portion, and therefore, an interval between a x-coordinate value of a starting point of the protruding portion and a x-coordinate value of an end point of the protruding portion in the x-axis direction is equivalent to 90°. Further, in the sectional view illustrated in FIG. 13(b), a height in the y-axis direction is equivalent to 2 mm. With the added dimensions illustrated in FIG. 14(b), the width of the expanded voxel data in the z-axis direction is, in the expanded voxel data illustrated in FIG. 11, equivalent to 10 mm, and the width of the protruding portion in the z-axis direction is equivalent to 5 mm.

Figure 15:
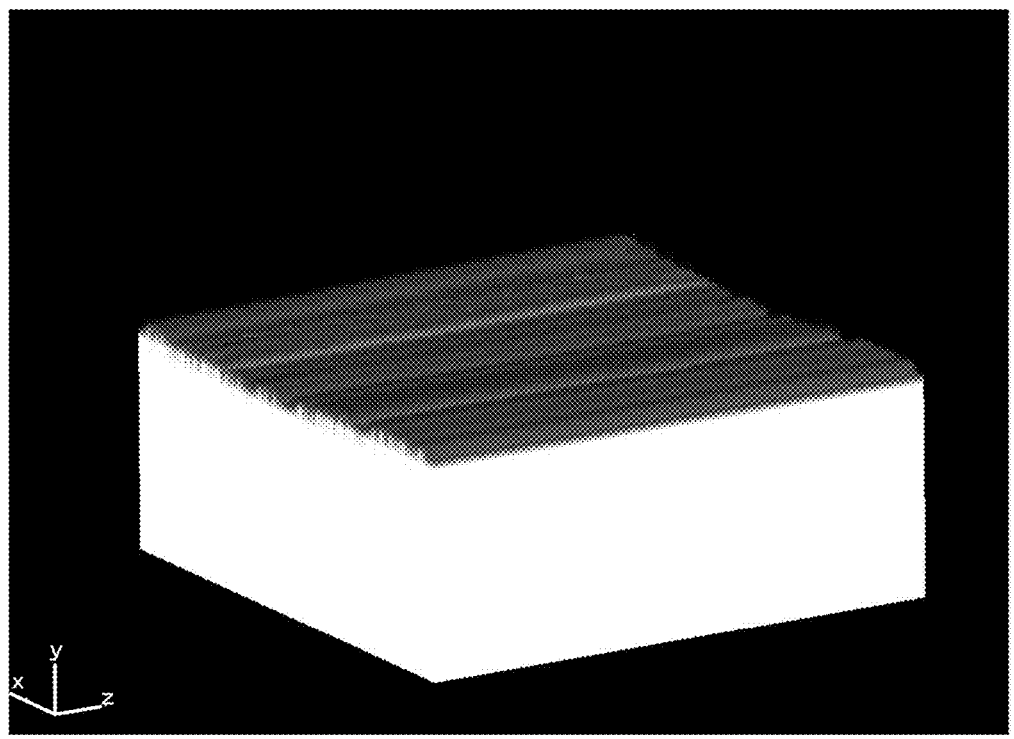
FIG. 15 is a view of an example of the expanded voxel data from which a protruding portion has been deleted.

The control device 102 performs, for the expanded voxel data, the processing of deleting the protruding portion shown on the expanded voxel data. Specifically, the control device 102 takes, in the expanded voxel data, two points of a starting point and an end point in the branched center line 7d direction, i.e., the z-axis direction, and then, interpolates a y-coordinate value between these two points by means of an interpolation method such as linear interpolation. Thus, the expanded voxel data illustrated in FIG. 11 is converted into expanded voxel data from which the protruding portion has been deleted as illustrated in FIG. 15.

After the protruding portion has been deleted from the expanded voxel data, the control device 102 converts such expanded voxel data from the orthogonal coordinate system into the cylindrical coordinate system, and in this manner, can acquire normal main vessel voxel data acquired by deletion of the protruding portion from the processing target voxel data.

Figure 16:
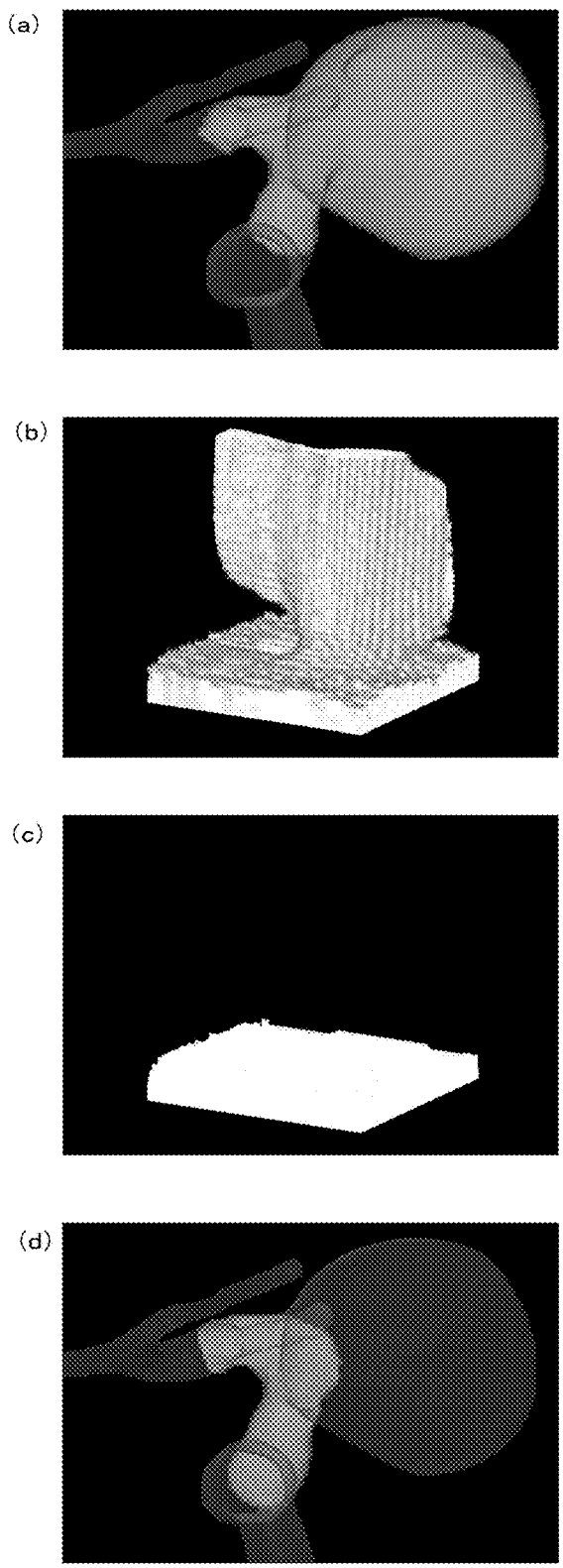
FIG. 16 is a view of the flow of image processing for generating normal main vessel voxel data from the processing target voxel data.

The flow of image processing for generating the normal main vessel voxel data from the processing target voxel data as described above will be described with reference to a specific example of FIG. 16. The control device 102 expands the processing target voxel data including the protruding portion as illustrated in FIG. 16(a) into the voxel data in the orthogonal coordinate system as illustrated in FIG. 16(b). Subsequently, the control device 102 takes, for deleting the protruding portion shown on the expanded voxel data, two points of the starting point and the end point in the z-direction on the expanded voxel data, and then, interpolates the y-coordinate value between these two points by linear interpolation. In this manner, the expanded voxel data is converted into the expanded voxel data from which the protruding portion has been deleted as illustrated in FIG. 16(c). After the protruding portion has been deleted from the expanded voxel data, the control device 102 converts such expanded voxel data from the orthogonal coordinate system into the cylindrical coordinate system. In this manner, the control device 102 generates the normal main vessel voxel data acquired by deletion of the protruding portion from the processing target voxel data as illustrated in FIG. 16(d).

The control device 102 may further calculate a difference between the processing target voxel data and the normal main vessel voxel data, thereby acquiring a difference image. In this manner, the control device 102 can produce voxel data with an extracted abnormally-protruding portion such as an aneurysm.

The control device 102 stores, in the storage device 103, the produced normal main vessel voxel data or the voxel data with the extracted abnormally-protruding portion. Moreover, the control device 102 outputs, in an automated manner or based on operation by the operator, the produced normal main vessel voxel data or the voxel data with the extracted abnormally-protruding portion to the display apparatus connected to the connection interface 101. This allows a doctor and the like to grasp a patient's normal main vessel shape or an abnormally-protruding portion shape, and therefore, use such a shape in diagnosis or medical treatment.

Figure 17:
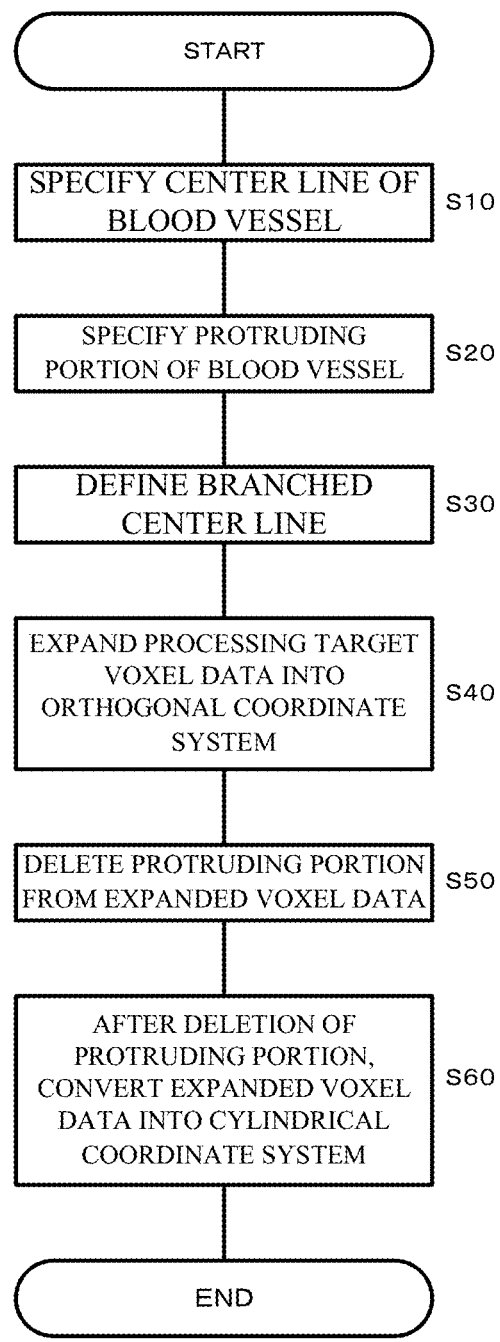
FIG. 17 is a flowchart of processing executed by the blood vessel image processing apparatus 100.

FIG. 17 is a flowchart of processing executed by the blood vessel image processing apparatus 100 in the present embodiment. The processing shown in FIG. 17 is, by the control device 102, executed as a program started when the operator of the blood vessel image processing apparatus 100 instructs execution of the program. Note that in the processing shown in FIG. 17, the above-described three-dimensional blood vessel data is stored in advance in the storage device 103.

At a step S10, the control device 102 reads the three-dimensional blood vessel data from the storage device 103, and produces the center line passing through the center of the blood vessel as described above. Subsequently, the processing proceeds to a step S20.

At the step S20, by the above-described method, the control device 102 specifies, based on the center line, the protruding portion of the blood vessel which is highly likely to be the abnormally-protruding region such as an aneurysm. Subsequently, the processing proceeds to a step S30.

At the step S30, the control device 102 specifies, as described above, the center lines branched from the center line 7a of the protruding portion, and these center lines are taken as the single center line to define the branched center line. Subsequently, the processing proceeds to a step S40.

At the step S40, the control device 102 converts the three-dimensional blood vessel data of the region including the branched center line into the processing target voxel data. The control device 102 performs, as described above, the voxel data expansion processing for the processing target voxel data, thereby converting such data into the voxel data in the orthogonal coordinate system. Subsequently, the processing proceeds to a step S50.

At the step S50, the control device 102 takes, as described above, two points on the z-axis on the expanded voxel data, and interpolates the y-coordinate value between these two points by means of the interpolation method such as linear interpolation. In this manner, the control device 102 deletes the protruding portion from the expanded voxel data. Subsequently, the processing proceeds to a step S60.

At the step S60, the control device 102 converts, after having deleted the protruding portion from the expanded voxel data, such expanded voxel data from the orthogonal coordinate system into the cylindrical coordinate system. Subsequently, the processing ends.

According to the present embodiment described above, the following features and advantageous effects can be obtained.

(1) The control device 102 specifies the center lines of the blood vessel based on the three-dimensional blood vessel data showing the three-dimensional shape of the blood vessel, specifies the center line of the protruding portion of the blood vessel from the above-described center lines, and specifies the center lines branched from the protruding portion center line. Then, the control device 102 defines, for the three-dimensional blood vessel data of the blood vessel corresponding to the branched center line, the cylindrical coordinate system using, as the coordinate axes, the blood vessel circumferential direction about the center line, the blood vessel radial direction from the center line, and the center line direction, thereby converting the blood vessel data in the cylindrical coordinate system into the blood vessel data in the orthogonal coordinate system. The control device 102 uses, on the blood vessel data in the orthogonal coordinate system, the coordinate value of the coordinate axis in the radial direction at the first coordinate value of the coordinate axis in the center line direction and the coordinate value of the coordinate axis in the radial direction at the second coordinate value of the coordinate axis in the center line direction, thereby interpolating the coordinate value of the coordinate axis in the radial direction between the first coordinate value and the second coordinate value. Then, the control device 102 converts, after interpolation, the blood vessel data in the orthogonal coordinate system into the blood vessel data in the cylindrical coordinate system. With this configuration, the protruding portion of the blood vessel such as an aneurysm can be detected by simple processing based on the center line of the blood data. Moreover, the protruding portion can be deleted from the blood vessel data in the orthogonal coordinate system by interpolation of the coordinate value in the blood vessel radial direction. Thus, as compared to the case of performing the image processing of deleting the protruding portion from the blood vessel data in the cylindrical coordinate system, the protruding portion of the blood vessel can be more accurately deleted by simpler processing. Further, the blood vessel data in the orthogonal coordinate system after interpolation is converted into the blood vessel data in the cylindrical coordinate system so that the normal main vessel shape after deletion of the protruding portion can be specified.

(2) The control device 102 calculates the difference between the three-dimensional blood vessel data and the blood vessel data in the cylindrical coordinate system after deletion of the protruding portion, thereby generating the three-dimensional data of the protruding portion. With this configuration, the shape of the abnormally-protruding region of the blood vessel such as an aneurysm can be specified.

(3) The control device 102 narrows the blood vessel in the concentric fashion from the outer peripheral side to the center side based on the three-dimensional blood vessel data, and when the line reaches the predetermined line thickness, the line is specified as the center line. With this configuration, the center line of the blood vessel on the three-dimensional blood vessel data can be accurately specified by simple processing.

(4) The control device 102 specifies the branching points of the center line, and specifies, as the center line of the protruding portion of the blood vessel, the center line having no branching point at least at one end. With this configuration, the center line of the protruding portion can be accurately specified considering the probability that the center line having no branching point and disconnected in the middle is highly likely to be the center line of the protruding portion.

(5) The control device 102 excludes, from the center lines, the center line contacting the outer periphery of the image region of the three-dimensional blood vessel data, thereby specifying the protruding portion of the blood vessel. Even when the center line has no branching point at one end, if the end of such a center line contacts the outer periphery of the image region of the three-dimensional blood vessel data, the blood vessel with such a center line is highly likely to be a normal blood vessel. Considering such a probability, the above-described center line can be excluded from protruding portion detection targets. As a result, erroneous detection of the normal blood vessel as having the protruding portion can be prevented.

(6) The control device 102 specifies, as the length of the center line, the length from the branching point to the point at which the center line is disconnected, and excludes the center line with the value equal to or less than the predetermined threshold to specify the protruding portion of the blood vessel, the value being obtained in such a manner that the specified length of the center line is divided by the radius from the center line to the outer periphery of the blood vessel. In the case of a small ratio of the thickness to the length of a blood vessel, such a blood vessel is highly likely to be a thin blood vessel disconnected in the middle. Thus, erroneous detection of such a thin blood vessel as having the protruding portion can be prevented.

Variations

Note that the following variations can be made to the blood vessel image processing apparatus 100 of the above-described embodiment.

(1) In the above-described embodiment, the following example has been described: the control device 102 takes two points of the starting point and the end point in the z-axis direction on the expanded voxel data, and interpolates the y-axis coordinate value between these two points by means of the interpolation method such as linear interpolation; and therefore, the protruding portion is deleted from the expanded voxel data. However, when a point with a smaller z-value than that at the starting position of the protruding portion shown on the expanded voxel data and a point with a greater z-value than that at the end position of the protruding portion shown on the expanded voxel data can be taken as the two z-axis direction points specified for interpolation, the protruding portion can be deleted from the expanded voxel data. Thus, the method for taking two points for interpolation is not limited to the method in which the starting point and the end point in the z-axis direction are taken.

(2) In the above-described embodiment, the following example has been described: the server apparatus having the configuration illustrated in FIG. 1 is used as the blood vessel image processing apparatus 100. However, the configuration of the blood vessel image processing apparatus 100 is not limited to the configuration illustrated in FIG. 1. As long as the apparatus can execute the processing in the above-described embodiment, other configurations may be employed. For example, the blood vessel image processing apparatus 100 may store, without including the storage device 103, various types of data in external storage equipment connected via a communication line, a cable, and the like. Moreover, in the above-described embodiment, the following example has been described: the display apparatus is connected via the connection interface 101. However, the display apparatus may be built in the blood vessel image processing apparatus 100.

Note that the present invention is not limited to the configuration of the above-described embodiment as long as the characteristic functions of the present invention are not impaired. Moreover, the above-described embodiment and the multiple variations may be combined together.

The disclosure of the following priority application is herein incorporated by reference:

Japanese Patent Application No. 2015-137485 (filed in Jul. 9, 2015)

LIST OF REFERENCE NUMERALS 100 blood vessel image processing apparatus
101 connection interface
102 control device
103 storage device

The invention claimed is:
1. A blood vessel image processing apparatus comprising:
a control device for executing program data:
a storage device storing the program data, the program data including:
a center line specifying unit configured to specify a center line of a blood vessel based on three-dimensional blood vessel data showing a three-dimensional shape of the blood vessel;
a protruding portion center line specifying unit configured to specify, as a protruding portion center line, a center line of a protruding portion of the blood vessel from the center line specified by the center line specifying unit;
a branched center line specifying unit configured to specify, as a branched center line, a center line branched from the protruding portion center line specified by the protruding portion center line specifying unit;
a conversion unit configured to define, for the three-dimensional blood vessel data of the blood vessel corresponding to the branched center line specified by the branched center line specifying unit, a cylindrical coordinate system using, as coordinate axes, a blood vessel circumferential direction about the branched center line, a blood vessel radial direction from the branched center line, and a direction of the branched center line, thereby converting the blood vessel data of the blood vessel corresponding to the branched center line in the cylindrical coordinate system into blood vessel data in an orthogonal coordinate system;
an interpolation unit configured to interpolate a coordinate value of the coordinate axis in the blood vessel radial direction between a first coordinate value and a second coordinate value, by using the blood vessel data converted into the orthogonal coordinate system by the conversion unit, each of the first coordinate value and the second coordinate value being a coordinate value of the coordinate axis in the direction of the branched center line;
using the interpolated coordinate value to delete the protruding portion;
an inverse conversion unit configured to convert, after interpolation by the interpolation unit, the blood vessel data in the orthogonal coordinate system into blood vessel data in the cylindrical coordinate system to generate normal main vessel voxel data; and
calculating a difference image between the three-dimensional blood vessel data and the normal main vessel voxel data to generate three-dimensional data of the protruding portion:
a display unit configured to display the blood vessel data converted in the cylindrical coordinate system by the inverse conversion unit or the calculated difference image, wherein
the protruding portion center line specifying unit specifies a branching point at which the center line specified by the center line specifying unit is branched, and specifies, as the protruding portion center line, a center line not having the branching point at least at one end,
specifies, as a length of the center line, a length from the branching point to a point at which the center line is disconnected, and
excludes a center line with a value equal to or less than a predetermined threshold to specify the protruding portion of the blood vessel, the value being obtained in such a manner that the specified length of the center line is divided by a radius from the center line to an outer periphery of the blood vessel.

2. The blood vessel image processing apparatus according to claim 1, further comprising
a protruding portion data generation unit configured to calculate a difference between the three-dimensional blood vessel data and the blood vessel data in the cylindrical coordinate system after inverse conversion by the inverse conversion unit, thereby generating three-dimensional data of the protruding portion.

3. The blood vessel image processing apparatus according to claim 1, wherein
the center line specifying unit narrows the blood vessel in a concentric fashion from an outer peripheral side to a center side based on the three-dimensional blood vessel data, and
when a line reaches a predetermined line thickness, the line is specified as the center line.

4. The blood vessel image processing apparatus according to claim 1, wherein
the protruding portion center line specifying unit excludes, from the center line specified by the center line specifying unit, a center line contacting an outer periphery of an image region of the three-dimensional blood vessel data, thereby specifying the protruding portion of the blood vessel.

5. A non-transitory computer readable medium storing a blood vessel image processing program for causing a computer to execute a center line specifying process of specifying a center line of a blood vessel based on three-dimensional blood vessel data showing a three-dimensional shape of the blood vessel;

a protruding portion center line specifying process of specifying, as a protruding portion center line, a center line of a protruding portion of the blood vessel from the center line specified by the center line specifying unit;

a branched center line specifying process of specifying, as a branched center line, a center line branched from the protruding portion center line specified by the protruding portion center line specifying unit;

a conversion process of defining, for the three-dimensional blood vessel data of the blood vessel corresponding to the branched center line specified by the branched center line specifying unit, a cylindrical coordinate system using, as coordinate axes, a blood vessel circumferential direction about the branched center line, a blood vessel radial direction from the branched center line, and a direction of the branched center line, thereby converting the blood vessel data of the blood vessel corresponding to the branched center line in the cylindrical coordinate system into blood vessel data in an orthogonal coordinate system;

an interpolation process of interpolating a coordinate value of the coordinate axis in the blood vessel radial direction between a first coordinate value and a second coordinate value, by using the blood vessel data converted into the orthogonal coordinate system by the conversion unit, each of the first coordinate value and the second coordinate value being a coordinate value of the coordinate axis in the direction of the branched center line;

using the interpolated coordinate value to delete the protruding portion;

an inverse conversion process of converting, after interpolation by the interpolation unit, the blood vessel data in the orthogonal coordinate system into blood vessel data in the cylindrical coordinate system to generate normal main vessel voxel data; and calculating a difference image between the three-dimensional blood vessel data and the normal main vessel voxel data to generate three-dimensional data of the protruding portion:

a display process of displaying the blood vessel data converted in the cylindrical coordinate system by the inverse conversion unit or the calculated difference image, wherein, at the protruding portion center line specifying process, a branching point at which the center line specified by the center line specifying process is branched is specified and a center line not having the branching point at least at one end is specified as the protruding portion center line, specifies, as a length of the center line, a length from the branching point to a point at which the center line is disconnected, and excludes a center line with a value equal to or less than a predetermined threshold to specify the protruding portion of the blood vessel, the value being obtained in such a manner that the specified length of the center line is divided by a radius from the center line to an outer periphery of the blood vessel.

6. The blood vessel image processing program according to claim 5, further comprising a protruding portion data generation process of calculating a difference between the three-dimensional blood vessel data and the blood vessel data in the cylindrical coordinate system after inverse conversion at the inverse conversion process, thereby generating three-dimensional data of the protruding portion.

7. The blood vessel image processing program according to claim 5, wherein at the center line specifying process, the blood vessel is narrowed in a concentric fashion from an outer peripheral side to a center side based on the three-dimensional blood vessel data, and when a line reaches a predetermined line thickness, the line is specified as the center line.

8. The blood vessel image processing program according to claim 5, wherein at the protruding portion center line specifying process, a center line contacting an outer periphery of an image region of the three-dimensional blood vessel data is excluded from the center line specified at the center line specifying process, and the protruding portion of the blood vessel is specified.

9. A computer-implemented method for processing blood vessel image, comprising:

a step of causing a center line specifying unit to specify a center line of a blood vessel based on three-dimensional blood vessel data showing a three-dimensional shape of the blood vessel;

a step of causing a protruding portion center line specifying unit to specify, as a protruding portion center line, a center line of a protruding portion of the blood vessel from the center line specified by the center line specifying unit;

a step of causing a branched center line specifying unit to specify, as a branched center line, a center line branched from the protruding portion center line specified by the protruding portion center line specifying unit;

a step of causing a conversion unit to define, for the three-dimensional blood vessel data of the blood vessel corresponding to the branched center line specified by the branched center line specifying unit, a cylindrical coordinate system using, as coordinate axes, a blood vessel circumferential direction about the branched center line, a blood vessel radial direction from the branched center line, and a direction of the branched center line, thereby converting the blood vessel data of the blood vessel corresponding to the branched center line in the cylindrical coordinate system into blood vessel data in an orthogonal coordinate system;

a step of causing an interpolation unit to interpolate a coordinate value of the coordinate axis in the blood vessel radial direction between a first coordinate value and a second coordinate value, by using the blood vessel data converted into the orthogonal coordinate system by the conversion unit, each of the first coordinate value and the second coordinate value being a coordinate value of the coordinate axis in the direction of the branched center line;

using the interpolated coordinate value to delete the protruding portion;

a step of causing an inverse conversion unit to convert, after interpolation by the interpolation unit, the blood vessel data in the orthogonal coordinate system into blood vessel data in the cylindrical coordinate system to generate normal main vessel voxel data; and calculating a difference image between the three-dimensional blood vessel data and the normal main vessel voxel data to generate three-dimensional data of the protruding portion;

a step of causing a display unit to display the blood vessel data converted in the cylindrical coordinate system by the inverse conversion unit or the calculated difference image, wherein the step of causing a branched center line specifying unit to specify includes specifying a branching point at which the center line specified by the center line specifying unit is branched, and specifying, as the protruding portion center line, a center line not having the branching point at least at one end, specifies, as a length of the center line, a length from the branching point to a point at which the center line is disconnected, and excludes a center line with a value equal to or less than a predetermined threshold to specify the protruding portion of the blood vessel, the value being obtained in such a manner that the specified length of the center line is divided by a radius from the center line to an outer periphery of the blood vessel.

10. The blood vessel image processing method according to claim 9, further comprising a step of causing a protruding portion data generation unit to calculate a difference between the three-dimensional blood vessel data and the blood vessel data in the cylindrical coordinate system after inverse conversion by the inverse conversion unit, thereby generating three-dimensional data of the protruding portion.

11. The blood vessel image processing method according to claim 9, wherein the center line specifying unit narrows the blood vessel in a concentric fashion from an outer peripheral side to a center side based on the three-dimensional blood vessel data, and when a line reaches a predetermined line thickness, the line is specified as the center line.

12. The blood vessel image processing method according to claim 9, wherein the protruding portion center line specifying unit excludes, from the center line specified by the center line specifying unit, a center line contacting an outer periphery of an image region of the three-dimensional blood vessel data, thereby specifying the protruding portion of the blood vessel.

* * * * *